(12) United States Patent
Arnone et al.

(10) Patent No.: US 6,828,558 B1
(45) Date of Patent: Dec. 7, 2004

(54) THREE DIMENSIONAL IMAGING

(75) Inventors: Donald Dominic Arnone, Cambridge (GB); Craig Michael Ciesla, Cambridge (GB)

(73) Assignee: Teraview Limited (GB)

( * ) Notice: Subject to any disclaimer, the term of this patent is extended or adjusted under 35 U.S.C. 154(b) by 43 days.

(21) Appl. No.: 10/009,249

(22) PCT Filed: Jun. 5, 2000

(86) PCT No.: PCT/GB00/02168

§ 371 (c)(1),
(2), (4) Date: Jul. 2, 2002

(87) PCT Pub. No.: WO00/75641

PCT Pub. Date: Dec. 14, 2000

(30) Foreign Application Priority Data

Jun. 4, 1999 (GB) .............................. 9913089
Jun. 9, 1999 (GB) .............................. 9913429

(51) Int. Cl.⁷ ................................................ G01J 5/02
(52) U.S. Cl. .............................. 250/341.1; 250/341.8; 250/358.1
(58) Field of Search ..................................... 250/341.1

(56) References Cited

U.S. PATENT DOCUMENTS

| | | | |
|---|---|---|---|
| 5,623,145 A | * | 4/1997 | Nuss ........................... 250/330 |
| 5,710,430 A | | 1/1998 | Nuss |
| 5,789,750 A | | 8/1998 | Nuss |
| 5,894,125 A | | 4/1999 | Brener et al. |
| 5,939,721 A | * | 8/1999 | Jacobsen et al. ............. 250/330 |
| 6,111,416 A | * | 8/2000 | Zhang et al. ................. 324/753 |

FOREIGN PATENT DOCUMENTS

| | | |
|---|---|---|
| EP | 0 828 143 A2 | 3/1998 |
| EP | 0 828 162 A2 | 3/1998 |
| EP | 0 864 857 A1 | 9/1998 |
| GB | 2 075 668 | 11/1981 |
| GB | 2 347 835 | 9/2000 |
| WO | WO 88/01485 | 3/1988 |

OTHER PUBLICATIONS

D.M. Mittleman et al: "T–ray Imaging" IEEE Journal of Selected topics in Quantum Electronics, vol. 2, No. 3, Sep. 1996.

S. Hunsche et al.: "THz Near–Field Imaging" Optics Communications 150 (1998) 22–26.

* cited by examiner

Primary Examiner—John R. Lee
Assistant Examiner—Phillip Johnston
(74) Attorney, Agent, or Firm—Ostrolenk, Faber, Gerb & Soffen, LLP

(57) ABSTRACT

A method and apparatus for imaging a sample, the method comprising the steps of: a) irradiating a sample to be imaged with a beam of pulsed electromagnetic radiation with a plurality of frequencies in the range from 25 GHz to 100 THz; b) detecting radiation which is both transmitted through and reflected from the sample; and c) generating an image of the sample from radiation detected in step (b). The method and apparatus can be used to generate a three-dimensional image of the sample and/or a compositional image of the sample.

28 Claims, 12 Drawing Sheets

THREE DIMENSIONAL IMAGING

The present invention relates to the field of imaging samples with radiation in the infra-red (IR) and Terahertz frequency range. More specifically, the present invention relates to apparatus and methods for imaging samples in three dimensions using electromagnetic radiation in the higher Gigahertz (GHz) and the Terahertz (THz) frequency ranges. However, in this type of imaging technology, all such radiation is colloquially referred to as THz radiation, particularly that in the range from 25 GHz to 100 THz, more particularly that in the range of 50 GHz to 84 THz, especially that in the range from 100 GHz to 50 THz.

Recently, there has been much interest in using THz radiation to look at a wide variety of samples using a range of methods. THz radiation has been used for both imaging samples and obtaining spectra. Work by Mittleman et al, IEEE Journal of Selected Topics in Quantum Electronics, Vol. 2, No. 3, September 1996, page 679 to 692 illustrates the use of using THz radiation to image various objects such as a flame, a leaf, a moulded piece of plastic and semiconductors.

THz radiation penetrates most dry, non metallic and non polar objects like plastics, paper, cardboard and non polar organic substances. Therefore, THz radiation can be used instead of X-rays to look inside boxes, cases etc. THz has lower energy, non-ionising photons than X-rays, hence, the health risks of using THz radiation are expected to be vastly reduced compared to those using conventional X-rays.

There is considerable interest in both medical and non-medical fields in the production of 3D images. For example, in dentistry the ability to produce 3D images of a tooth would enable dentists to locate exactly where caries (tooth erosion) or other abnormalities occur in the tooth. Most of the conventional imaging modalities—X-Ray, MRI, etc.—are handicapped by the fact that they can intrinsically only produce 2D images, with 3D images possible only by translating the patient or body part through the X-Ray beam or through the magnetic field in the case of MRI.

The use of THz for imaging the internal structure of a flat object (a floppy disc) has been described in EP 0 864 857. Here, the inventors measured reflection of a beam of THz radiation to produce an image of the internal structure of the sample.

However, this method is not suitable for obtaining 3D images of objects where the front and back surfaces are curved. Most objects have interfaces and/or external surfaces which are non-planar, i.e. have substantial radii of curvature. If a beam is reflected from a curved surface, it is reflected at an angle to the incident beam. The method of EP 0 864 857 does not show how to obtain an image when the radiation is reflected from a curved surface.

Also, partially absorbing objects give rise to weak reflections from buried layers resulting in long absorption lengths for certain reflected pulses. This limits the thickness of objects which can be accurately imaged in 3D using THz reflection data alone.

The present invention addresses the above problems in a first aspect provides a method of imaging a sample, the method comprising the steps of:
  (a) irradiating the sample to be imaged with an irradiating beam of pulsed electro magnetic radiation with a plurality of frequencies in the range from 25 GHz to 100 THz,
  (b) detecting both the radiation transmitted through the sample and the radiation reflected by the sample;
  (c) generating an image of the sample from the radiation detected in step (b).

Collecting both the reflected and transmitted radiation allows a greater range of curved surfaces to be measured. Hence, the method of the present invention is capable of imaging a sample of virtually any shape. The collection of both the transmitted and reflected radiation also allows a compositional image of the sample to be obtained.

Radiation transmitted through the sample is primarily used to determine the sample shape and the composition. Radiation which is reflected from the sample is primarily used to measure the positions of dielectric surfaces within the sample in addition to giving shape information. This technique allows the curvature of both internal and external surfaces to be measured. Thus, using both reflected and transmitted radiation is an extremely powerful tool to determine the three dimensional compositional structure of the object.

Taking a uniform sphere as a simplified example. In such an example there are no internal interfaces. Therefore, the pulse is at either transmitted through the sphere or will be reflected on entering or exiting the sphere. Subdividing the sample into a 2D array of pixels and measuring the time of flight of the transmitted pulse through the sample will allow the thickness of the sample to be determined at each pixel. However, this will not determine the shape of the sample as the position and shape of the front interface is not known. The shape of the front interface can be determined from the time of flight of the pulse which is reflected on entering the sphere. Thus, it is possible to obtain information about the shape of a sample by plotting the difference between the time of flight of the transmitted and reflected pulses relative to the time of flight of the reflected pulse.

Therefore, the step of generating the image preferably comprises the steps of calculating the time of flight of the pulse transmitted through the sample; calculating the time of flight of a pulse reflected from an interface or surface of the sample; and plotting the difference or a function of the difference of the time of flight of the transmitted pulse and the reflected pulse relative to the time of flight of the reflected pulse.

A function of the difference can be plotted in order to correct for variations in the refractive index of the sample.

In the case of a sphere, theoretically, the pulse reflected on exiting the sphere could be used to determine the shape of the sample in conjunction with the pulse reflected on entering the sphere. However, it is not desirable to use the pulse reflected on exiting the sample as it will be scattered through a fairly large angle, possibly outside the range of the detector. Further, as the reflected pulse has passed twice through the sample, it is likely to be very weak.

The present invention can be used to image far more complex objects than the above uniform sphere. As mentioned above, it is difficult to detect a reflected pulse from the interfaces which are deepest within the sample. Such a complex sample is measured using a reflected radiation detector (or detectors) which is located at the same side on the sample as the incident THz pulse and a transmitted radiation detector (or detectors) which is located on substantially the opposite side of the sample to the incident THz pulse. In a sample with many interfaces, some of the radiation detected by the transmitted radiation detector will have been transmitted through the whole of the sample. However, some of the radiation collected will have undergone multiple reflections. For example, radiation can be reflected back into the sphere from the sphere's external surface onto an internal interface. The pulse is then reflected for a second time at the internal interface out of the sphere. This reflected pulse will be collected by the transmitted radiation detector. The position of interfaces deep within the sample can be determined by looking at the signal due to such doubly reflected pulses or pulses which have undergone an even number of reflections.

Therefore, preferably, the step of generating the image comprises the step of extracting the parts of the detected transmitted pulse which are due to an even number of reflections within the sample, and determining the position of an interface using the said signal caused by said even number of reflections.

In order to be able to directly compare the reflected and transmitted signals, it is preferable if a reference signal is provided. Said reference signal is preferably provided by a reflection off an object which is a known distance with respect to either the source of THz radiation or the sample being imaged. The reflection may be taken from an object, which is preferably planar located between the source of the radiation and the sample being imaged and is preferably taken from a reflection off a component of the source itself.

In addition to collecting both transmission and reflection data, it is preferable if the resolution of the system is not limited by the diffraction limit. Therefore, it is preferable if the beam which irradiates the sample has a beam diameter which is smaller than the smallest wavelength of radiation in the pulse of electromagnetic radiation.

To obtain an image of the whole sample, the sample is preferably subdivided into a 2 dimensional pixel array. The radiation which is either reflected by or transmitted through each pixel is detected. The image is then generated pixel by pixel.

Preferably, the sample which is to be imaged is placed on a motorised stage, which can be stepped in the both the x and y directions. An image of the entire sample can then be generated pixel by pixel.

Due to the beam diameter being smaller than the wavelength of the radiation, the present invention utilises near-field techniques. Hence, the spatial resolution is not determined by the focused spot size of the THz beam.

The beam of pulsed radiation which is used to irradiate the sample is preferably generated by an emitter which has non-linear optical properties. The material of the emitter is preferably chosen such that when the emitter is irradiated with radiation with a predetermined input frequency or frequencies, the emitter emits a beam with the desired output frequency or frequencies i.e. a frequency or frequencies in the range from 50 GHz to 84 THz. The frequency of the emitted beam is determined by both the frequency or frequencies of the input radiation and the non-linear properties of the emitter itself.

The emitter can be a semiconductor crystal with non-linear optical properties type which allow visible pulses of light (i.e. pulses with wavelengths in the range from 0.3 $\mu$m to 1.5 $\mu$m) to be converted to pulses with a wavelength in the range from 50 GHz to 84 THz. The emitter may be chosen from a wide range of materials, for example, $LiIO_3$, $NH_4H_2PO_4$, ADP, $KH_2PO_4$, $KH_2AsO_4$, Quartz, $AlPO_4$, ZnO, CdS, GaP, GaAs, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, DAST (4-N-methylstilbazolium) or Si. Other types of emitter could be used, for example, photoconductive antennas which emit radiation in the desired frequency range in response to irradiation by an input beam having a different frequency and upon the application of a bias to the antenna.

In the case of an emitter which has non-linear optical properties, to keep the input beam in phase with the emitted beam (THz beam), the emitter preferably comprises phase matching means. The phase matching means can be of the type for enhancing the phase matching between at least two different frequency signals propagating in the emitter in response to illumination by at least one incident beam of radiation, the phase matching means having a spatial rotation in its refractive index along a component of the incident radiation beam.

Preferably, the diameter of the beam which irradiates the sample is determined by the diameter of the visible or near-infrared beam which irradiates the emitter. In this situation, there is no need to have extra active optical components between the sample and the emitter to focus the beam. However, in such an arrangement, the sample needs to be positioned close to the emitter. The sample may be mounted directly onto the emitter. Alternatively, the sample may be mounted in very close proximity to the semiconductor emitter. For example, between 10 and 500 $\mu$m. Also, the sample may be mounted on a passive optical component which is invisible to THz radiation i.e. a window. The window does not serve to focus the beam.

It may be preferable to separate the emitter and the sample, if the emitter comprises a toxic material, for example, ZnTe.

In the method of the present invention, both transmitted and reflected radiation pulses are measured. When an emitter of the type described above is used, the reflected THz passes must pass back through the emitter (without significant losses) before they are collected as reflected THz for analysis. Therefore, preferably, the emitter is transparent to THz radiation or at least to the radiation of the irradiating beam. Semiconductors with a low carrier doping concentration are useful for this aspect.

The present invention uses both transmission and reflection in order to determine the internal and external shape of the sample. The need to measure, at the reflected signal detector, the pulse which has been reflected once from the curved interfaces located deep within the sample is avoided. However, the reflected signal will be measured from the curved interfaces which are close to the front interfaces. In order to permit a range of sample sizes and radii of surface or interface curvatures which are close to the front of the sample to be measured, the emitter must also be sufficiently large to allow all of the reflected beams to pass back through the emitter. If the emitter is too small, or if the imaging takes place too close to the edge of the emitter, some of the reflections may be blocked by the mount of the emitter. To allow a smaller crystal to be used, it is preferable if just the sample moves in order to image the area of the sample. As the sample moves relative to both the emitter and the input beam of the emitter, a smaller emitter can be used.

To further reduce the size of the emitter, the emitter may be mounted on a "THz window". The window material could be for example polyethylene, polythene, high-resistivity silicon, Z-quartz or TPX (poly-4-methylpentene-1), it must be at least substantially transparent to the irradiating beam. The window would preferably be thin, for example, between 50 and 300 microns. This is to ensure that the THz beam diameter is still smaller than the shortest wavelength component when the THz beam reaches the sample. The size of the window is large enough to allow all of the reflected beams to be collected with negligible loss. As the emitter is provided on the window which is substantially transparent to THz, the THz can pass through the mount for the emitter.

Also, using conventional coherent THz detection methods, for example, electro-optic sampling and photoconductive detection, the THz beam must be focused to a point and thus information is lost about the path the different THz beams take following reflection. This problem can be addressed by using a CCD camera. Therefore, it is preferable if a CCD camera is used in the detection the reflected THz beams. This detection method allows reflection techniques to map out the shape of curved surfaces, also, it would be possible to map out differences in shape between internal and external dielectric surfaces.

It should be noted that the CCD camera would probably not be used to detect the THz directly, instead the THz would be converted to a visible or near IR radiation an electro-optical component, the near IR visible radiation would then be collected by the CCD. Preferably, this conversion to IR or visible radiation would be achieved by passing a polarised reference beam with the THz beam through a material which supports the AC pockets effect. The light emitted by the material is then passed through a polariser to the CCD. Only light which has had its polarisation rotated by the THz signal will be transmitted be the polariser into CCD.

Also, when collecting the output light using an off axis parabolic mirror, there is a slight time delay due to the different optical path lengths between the centre and the edge of the mirror. Consequently, the different path lengths of the reflected beams cause the pulses to arrive at different times at the detector. This causes a problem, because it is not easy (if at all possible) to distinguish between a time-shift of a pulse due to the position of an internal dielectric layer and a time shift which is a combination between a reflection from the sample and a different path length due to one of the optical mirrors. This problem can also be addressed by the use of a CCD camera as a detector. A CCD camera can be used to image a 2D region containing all the reflected THz beams, both the temporal and spatial shift if the THz can be measured. In other words, more exact information about the sample can be gained by using a CCD camera.

The CCD technique can be used to collect radiation which is both transmitted and reflected from the sample. As in many situations, the transmitted beam may also be transmitted off axis.

In the method of the present invention, data can be derived by using the time-of-flight method. As the enters the sample, its velocity changes due to variations in the refractive index of the sample. Thus, by measuring the time of flight of the pulse through the sample, an image of the sample shape can be obtained using transmission.

Using the frequency domain analysis techniques of UK application no 9940166.7, the composition of the structure can be determined. In this application, a single frequency from the plurality of transmitted or reflected plurality of frequencies is used to generate the image. In some cases, a narrow range of frequencies or a selection of specific frequencies or frequency ranges is studied. A selected frequency range is taken to be a frequency range typically less than a third of the total range of the passed electromagnetic radiation used to irradiate the sample. More preferably, the selected frequency range is less than 10% of the total frequency range of the passed electromagnetic radiation used to irradiate the sample.

For example, water is a strong absorber of THz radiation. There are "windows" in the water absorption spectra from 50 GHz to 500 GHz, from 30 THz to 45 THz and from 57 THz to 84 THz. If the sample is irradiated with a range of frequencies from 50 GHz to 84 THz, it may be preferable to generate the image using one or more of the following selected frequency ranges: 50 GHz to 500 GHz, 30 THz to 45 THz and 57 THz to 84 THz. The image may be generated by integrating over the selected frequency range.

Thus, by analysing the transmitted information as above, an image can be created by a single frequency or a selected frequency range. Also, a plurality of images may be derived from a plurality of frequencies or a single image may be derived from two or more distinct frequencies. This is a very powerful analysis and allows variations in the composition of the material to be determined.

The image or images may be generated in a number of ways. For example, a sequence of images may be generated from a plurality of different frequencies.

In general, the present invention will be performed using imaging apparatus which is configured to detect temporal data at each pixel. Preferably, the data is Fourier transformed to give the complex THz electric field in the frequency domain E ($\omega$).

The image can be obtained in a number of ways from the complex THz electric field E($\omega$), e.g.:

(i) The power spectrum $P_{sample}(\omega)$ of the sample and the power spectrum $P_{ref}(\omega)$ of the reference signal may be calculated. The image could then be generated by plotting the difference between the two Power spectrums for a given frequency for each pixel at a selected frequency over integrated over a selected frequency range.

(ii) The power spectrum $P_{sample}$ of the sample and the reference power spectrum $P_{ref}$ may be divided to give the transmittance. The transmittance may then be plotted for each pixel at a selected frequency over integrated over a selected frequency range.

(iii) The frequency dependent absorption coefficient $\alpha(\omega)$ may be calculated from the complex electric field E($\omega$) and plotted for each pixel at a selected frequency over integrated over a selected frequency range.

(iv) The frequency dependent refractive index $\eta(\omega)$ may also be calculated from the complex electric field and plotted for each pixel at a selected frequency over integrated over a selected frequency range.

The detected temporal electric field contains both phase and amplitude information which give a complete description of the complex dielectric constant of the medium in the beam path. The sample to be characterised is inserted into the beam and the shape of the pulses that have propagated through the sample or have been reflected from the sample are compared with the reference temporal profile acquired without the sample. The ratio of the complex electric field E($\omega$) and the reference signal $E_{ref}(\omega)$ is calculated to give the complex response function of the sample, S($\omega$). In the most simple case, the complex response function is given by:

$$S(\omega) = \frac{E(\omega)}{E_{ref}(\omega)} \propto \exp\left(\frac{i\omega d}{c}(\eta(\omega) - 1)\right)\exp(-\alpha(\omega)d) \quad (1)$$

where d is the sample thickness, c is the velocity of light in vacuum, $\eta$ is the refractive index and $\alpha$ is the absorption coefficient. The experimental absorption coefficient $\alpha(\omega)$ and the refractive index $\eta(\omega)$ may then be easily extracted from the magnitude M($\omega$) and the phase $\phi(\omega)$ of S($\omega$), respectively, according to $$\alpha(\omega) = -\frac{1}{d}\ln(M(\omega)) \quad (2)$$

$$\eta(\omega) = 1 + \left(\frac{c}{\omega d}\right)\phi(\omega) \quad (3)$$

Additional terms may be included in equations (1) to (3) to account for reflections at dielectric interfaces of a sample, thus allowing accurate analysis of multilayered samples.

These parameters are simply related to the complex dielectric function $\in(\omega)$ of the sample $$\in(\omega)=(\eta(\omega)+ik(\omega))^2=(\eta(\omega)+i\alpha(\omega)c/2\omega)^2 \qquad (4)$$

The data derived as discussed in (i) to (iv) above, may be directly plotted either as a colour or a grey scale image where the colour or shade of grey of each pixel represents a given magnitude.

Instead of a single frequency, a selected frequency range could be chosen and the result and data of (i) to (iv) integrated over that range. The integrated data could then be plotted.

It may also be preferred to subdivide the magnitude of the data process in accordance with any of (i) to (iv) above into various bands. For example, all data below a certain value could be assigned the value 0, all data in the next magnitude range could be assigned the value 1, etc. These ranges may have equal widths in magnitude or they may have different widths. Different widths may be preferable to enhance contrast e.g. to emphasise contrast in regions of the sample where there is little variation in the sample absorption of Thz.

Preferably, the present invention uses two or more frequencies. The data from say two frequencies is processed in accordance with any of (i) to (iv) above. The data is then banded as described for a single frequency above.

The data may be split into two hands, one assigned the value "0" and the other "1". The data from both frequencies can then be added together using a rule such as a Boolean algebraic expression e.g. AND, OR, NOT, NAND, XOR, etc.

Of course, the present invention also allows images to be compared from two different frequencies. This may be particularly useful to identify a substance where the absorption to THz changes over a certain frequency range.

Thus, complex images can be produced. This system is particularly useful in the detection of breast cancer where both spatial information and compositional information concerning the 3D structure of the breast can be derived. Also, the present invention can be used to image teeth and bone.

The method of the present invention allows the internal composition, shape and the position of the internal surfaces to be determined. Hence, a three dimensional image of the sample can be produced from the methods of the three aspects of the present invention. In a second aspect, the present invention provides an apparatus comprising:

a) means for irradiating a sample to be imaged with an irradiating beam of pulsed electromagnetic radiation with a plurality of frequencies in the range from 25 GHz to 100 THz;

b) means for detecting radiation which is both transmitted through and reflected from the sample; and c) means for generating an image of the sample from radiation detected in step (b).

For the reasons described above, it is preferable if the imaging is performed in the near-field regime. Therefore, it is preferable if the means for radiating a sample comprises an emitter for emitting a beam of radiation with a plurality of frequencies in the range from 25 GHz to 100 THz, the emitter having optical non linear properties, such that when the emitter is irradiated with an input beam with a frequency in the visible or near infra-red frequency ranges, a beam is emitted with frequencies in the range from 25 GHz to 100 THz. Preferably, the input beam of pulsed radiation has a diameter which is smaller than that of the smallest wavelength of the emitted beam.

To image the sample, the sample should be stepped pixel by pixel in two orthogonal directions. Therefore, it is preferable that the apparatus further comprises a motorised stage configured so that it can be stepped pixel by pixel into two orthogonal directions.

The sample itself can be mounted on the motorised stage. Alternatively, both the sample and the emitter can be mounted on the motorised stage.

The present invention will now be described with reference to the following preferred non-limiting embodiments, shown in the following drawings in which.

Figure 1:
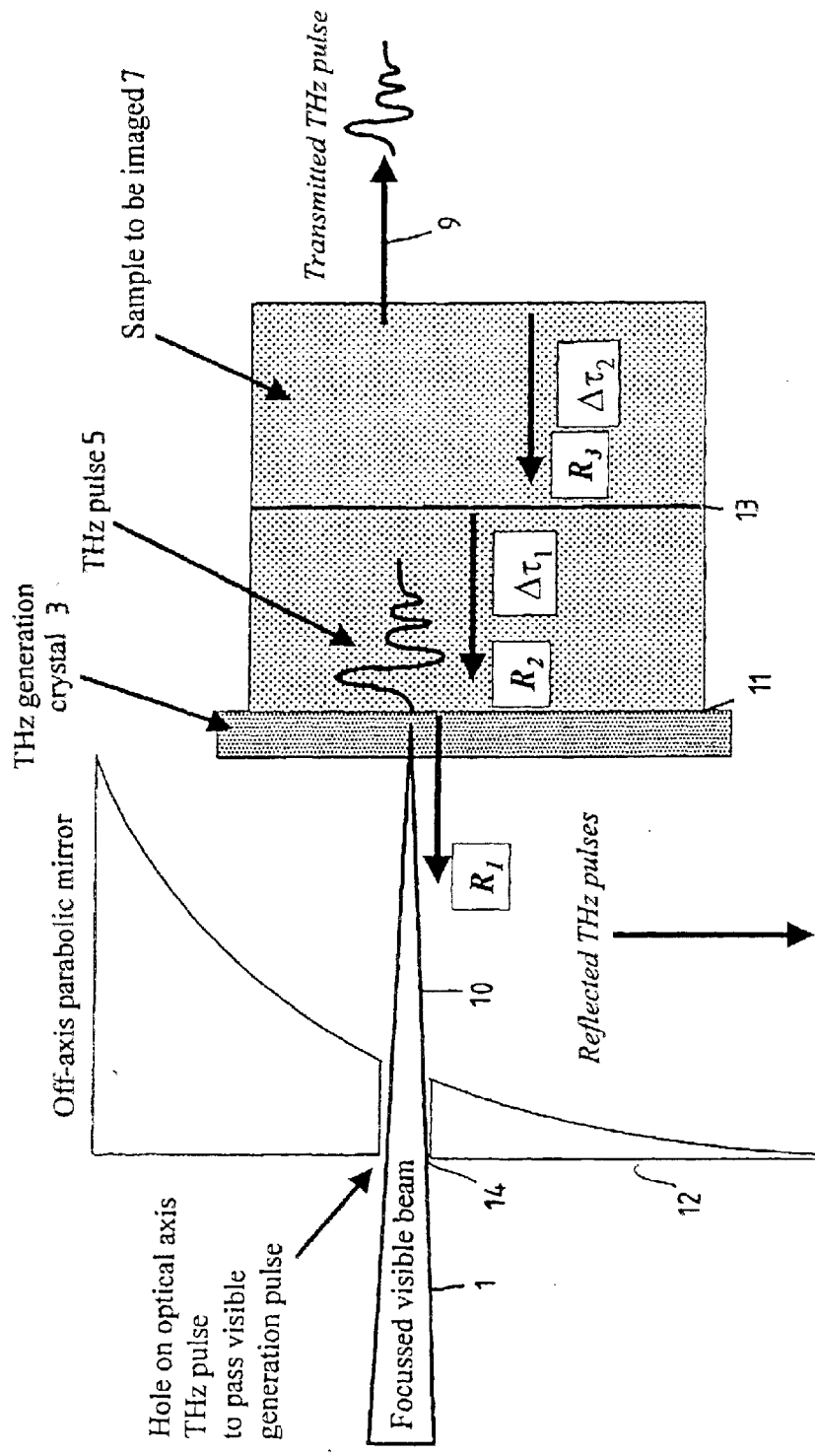
FIG. 1 shows a schematic near-field transmission and reflection imaging system according to an embodiment of the present invention.

FIG. 1 is a schematic of a near-field transmission and reflection imaging system. A focused visible beam (which has a wavelength in the visible electro-magnetic region i.e. typically between 0.3 $\mu$m to 1.5 $\mu$m) 1 is focused onto a THz emitter 3. The THz generation crystal is a crystal with non-linear properties which will emit radiation in the THz regime (50 GHz to 84 THz) when irradiated by visible light. The THz pulse 5, is emitted from the THz generation crystal 3. The actual frequency of the emitted beam is determined by the frequency of the input radiation and the physical properties of the emitter itself. An emitted beam with the desired frequency range can be obtained by appropriate selection of the emitter material and the frequency of the input radiation.

The diameter of the input which impinges on the THz generation crystal, is smaller than that of the smallest wavelength which will be generated in the THz pulse from the emitter 3. The sample 7, is directly mounted onto the emitter 3. Therefore, the sample is imaged with a beam of THz radiation which has a beam diameter which is less than that of the smallest wavelength of the THz light. Thus, the resolution of the image obtained from the sample will not be limited by the diffraction limit.

Some of the THz pulse will be transmitted through the sample 7. The transmitted THz is denoted by reference numeral 9. THz pulses will also be reflected from the sample 10. In this specific example, the first reflection of the THz pulse 5 occurs at the interface 11 between the sample 7 and the emitter 3. A second dielectric interface 13 within the sample 7 causes reflection $R_2$ which is the second reflected THz pulse. This pulse will be reflected at a time $\Delta\tau_1$ the third reflection $R_3$ occurs as the THz pulse leaves the sample 7. By collecting both the reflected and transmitted pulses, considerable detail about sample 7 can be determined.

The reflected THz pulses 10 are collected by off axis parabolic mirror 12. The passes are then reflected into a detector (not shown). The off axis parabolic mirror 12 has a hole 14 for transmitting the focused visible beam 1 from the source (not shown) to the emitter 3.

Figure 2:
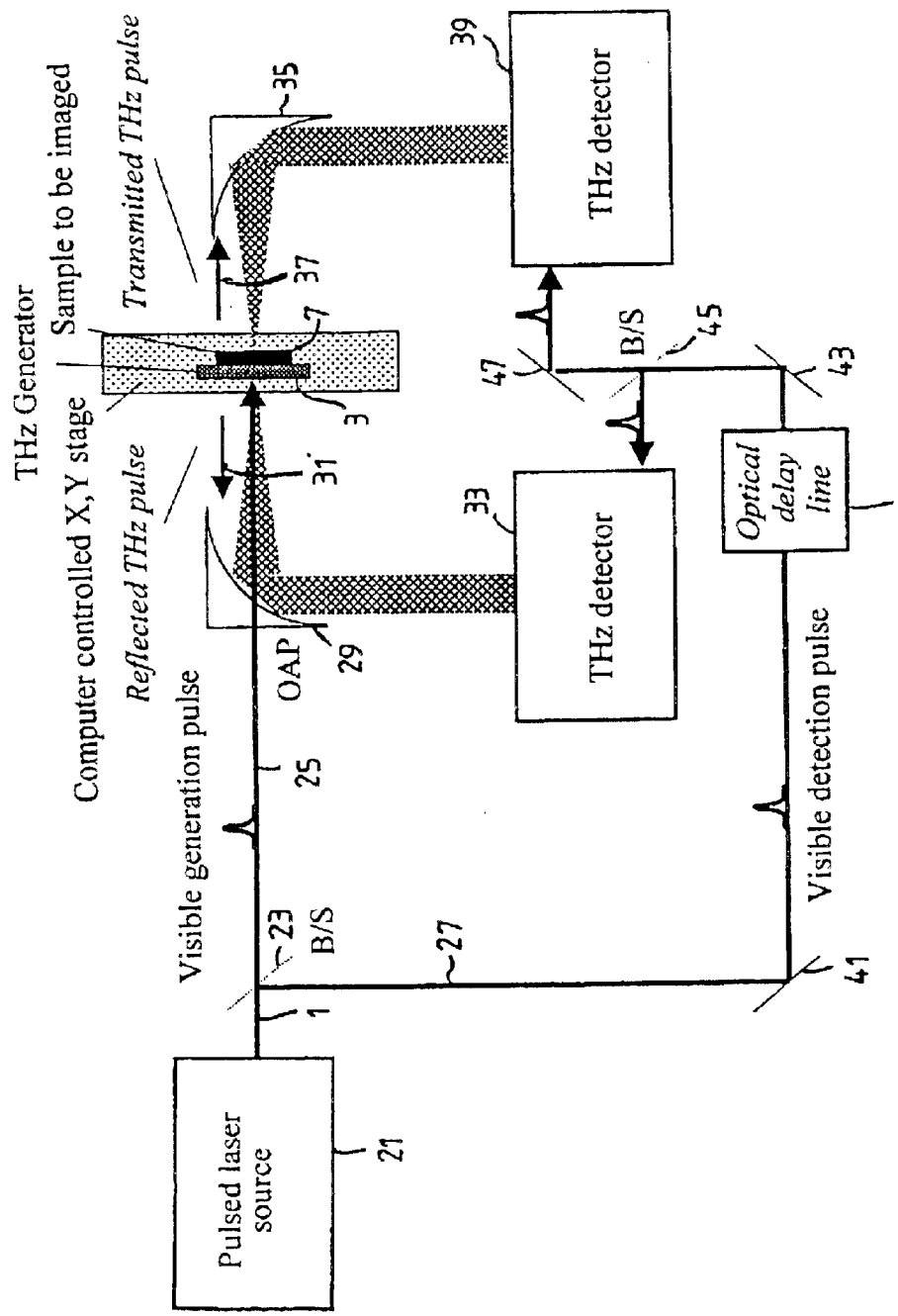
FIG. 2 shows the system of FIG. 1 with a source and detectors for both the transmitted and reflected radiation.

FIG. 2 shows a complete system. For convenience, like numerals denote like components on the previous and remaining figures. Pulse laser source 21 provides the beam of visible light 1. The beam of light 1 impinges on beam splitter 23. The beam splitter may be a half silvered mirror or the like. Beam splitter 23 passes a part of the visible pulse 25 towards the emitter 3 and a second part of the visible pulse 27 is reflected towards the detection mechanism. This beam 27 will eventually be used as a reference beam in the detection mechanism. Initially looking at the visible beam 25 which is used for generating the THz beam, this is first passed through an off axis parabolic mirror 29. The off axis parabolic mirror 29 has a hole to allow transmission of the visible pulse therethrough. The pulse is then directed onto the emitter 3 as shown in FIG. 1.

As explained above in relation to FIG. 1, the THz pulse 5 is reflected off the external surfaces and dielectric internal surfaces of the sample 7. This reflected pulse 31 is then collected by off axis parabolic mirror 29 (this is the same mirror through which the visible pulse 25 passes). The mirror 29 reflects the pulse into THz detector 33 which is used to produce the image. A second off axis parabolic mirror 35 is used to collect the transmitted THz pulse 37 from the sample 7. The off axis parabolic mirror 35 directs the transmitted pulse onwards transmitted pulse THz detector 39.

Visible pulse 27 is directed via mirrors, 43, 45 and 47 into THz detectors 33 and 39. An optical delay line 49 is provided to synchronise the visible pulse 27 with the collected reflected and transmitted THz radiation. As the reflected and transmitted THz radiation passes through the sample, the pulse is delayed, the optical delay line compensates for this effect.

Figure 3:
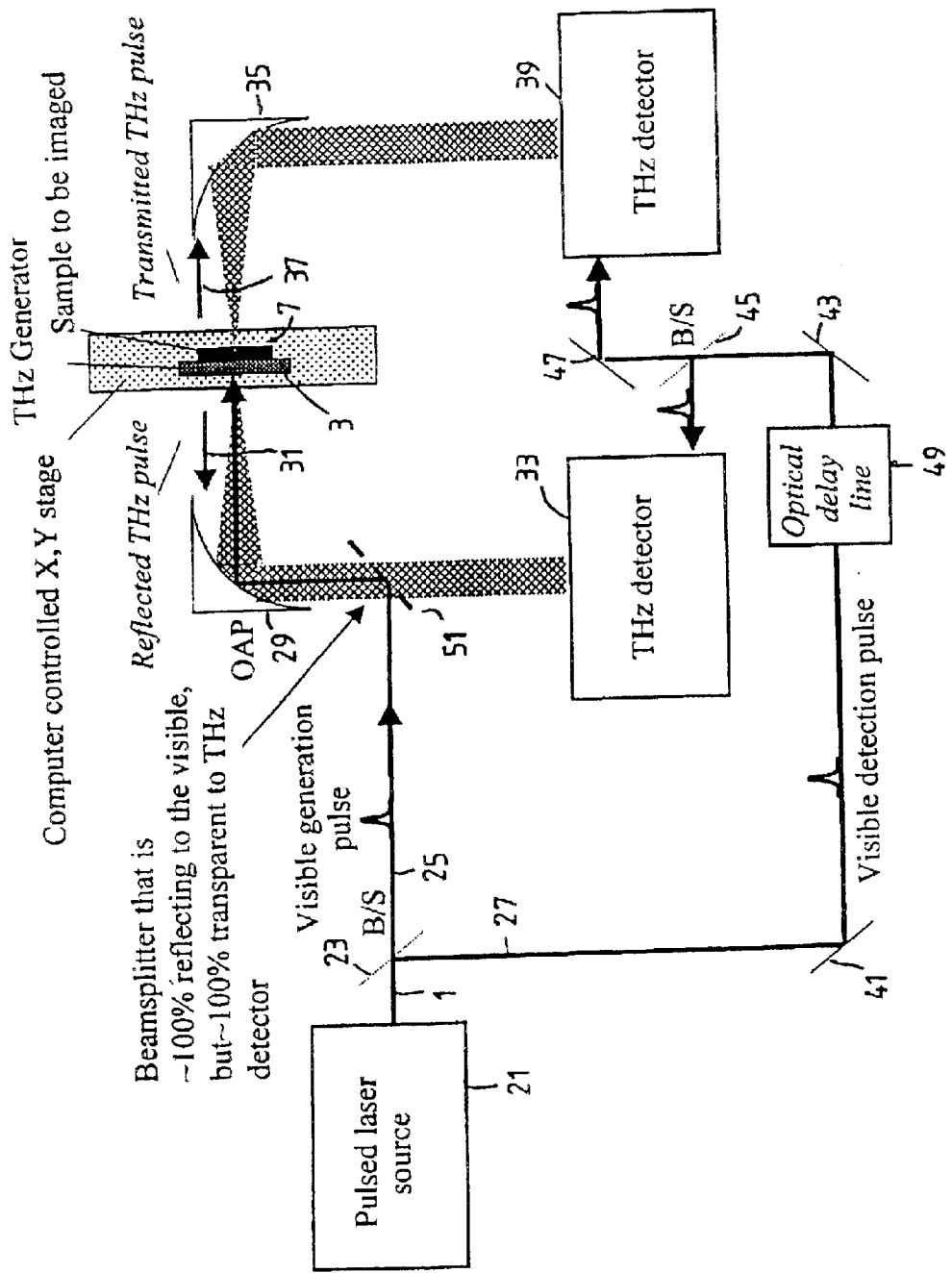
FIG. 3 shows a variation on the imaging system of FIG. 2.

FIG. 3 shows a variation of the imaging system of FIG. 2. FIG. 3, is very similar to FIG. 2. However, here, the visible beam 25 impinges on a dichoric beam splitter 51. The beam splitter is ideally 100% reflective to the visible light but 100% transparent to the reflected THz beam. In this arrangement, the dichoric mirror 51 reflects the beam onto the off axis parabolic mirror 29. The off axis parabolic mirror then directs the visible beam onto the emitter 3. As the visible beam 25 is being reflected from the off axis parabolic mirror, the off axis parabolic mirror 29 can be used to focus the beam to a small diameter (about 100 microns) on the generation crystal 3.

The reflected THz pulse 31 is collected in the same manner as described for FIGS. 1 and 2, the reflected pulse as collected by off axis parabolic mirror 29. The off axis parabolic mirror 29 directs the reflected pulse 31 onto dichoric mirror 51. The dichoric mirror is transparent to THz therefore it transmits the pulse 31 into THz detector 33.

The collection of the transmitted radiation 37 and the direction of the reference beam 27 into detectors 33 and 39 is identical to that described in FIG. 2.

Figure 4:
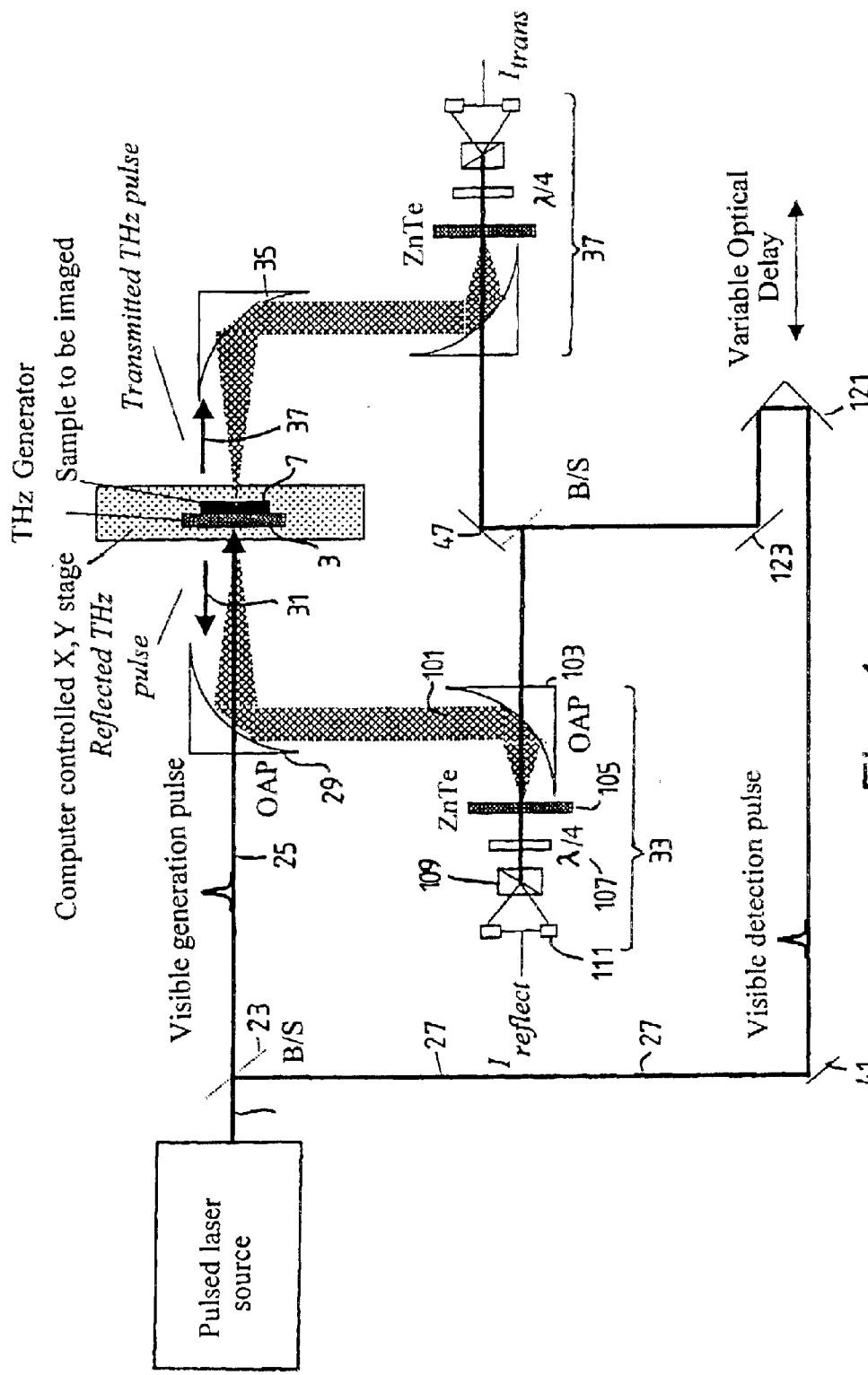
FIG. 4 shows the imaging system of FIG. 2 with details of the detectors.

FIG. 4 shows a full detection system using electro-optical detection. The system is largely identical to that of FIG. 2. However here, the THz detectors 33 and 39 are shown in more detail. Detection systems 33 and 39 are identical. Therefore, for simplicity only detection system 33 will be described.

In the detector 33 the THz beam carrying the reflected sample information 101 and a visible light beam 27 are combined using an off axis parabolic mirror 103. The off axis parabolic mirror 103 has a hole for the transmission of the visible beam 27 therethrough. Both the visible beam 27 and the reflected beam 101 are then directed onto a THz detection crystal 105. The visible light beam 27 acts as a reference beam which is incident on the detection crystal 105. Each of the axes has distinct refractive indices $n_o$ and $n_e$ along the ordinary and extraordinary axis of crystal 105 respectively. In the absence of a second THz radiation beam 101, the linearly polarised reference beam 27 passes through the detection crystal 105 with negligible change to its polarisation.

The applicant wishes to clarify that although the angle through which the polarisation is rotated by is negligible, the linearly polarised beam can become slightly elliptical. This effect is compensated for by a variable retardation wave plate, e.g. a quarter wave plate 107. The emitted beam is converted into circularly polarised light using the quarter wave plate 107. This is then split into two linearly polarised beam by a beam splitter such as a Wollaston prism 109 which directs the two orthogonal components of the polarised beam onto a balanced photodiode assembly 111. The balanced photodiode signal is adjusted using wave plate 107 such that the difference in outputs between the two diodes is zero.

However, if the detector 107 also detects a secondary beam 101 (in this case a beam with a frequency in the THz range) as well as the reference beam, the angle through which the polarisation is rotated is not negligible. This is because the THz electric field modifies the refractive index of the visible (fundamental) radiation along one of the axes $n_e$, $n_o$. This results in the visible field after the detector 105 being elliptical and hence the polarisation component separated by the prism 109 are not equal. The difference in the signal between the diode outputs gives a detection signal.

The reference beam 27 and the THz beam 101 should stay in phase as they pass through the crystal 105. Otherwise, the polarisation rotation is obscured. Therefore, the detection crystal 105 has phase matching means to produce a clear signal.

The optical delay is introduced by cube mirror 121 and plane mirror 123. Cube mirror 121 moves in and out to vary the length of the optical path and of the reference beam 27.

Figure 5:
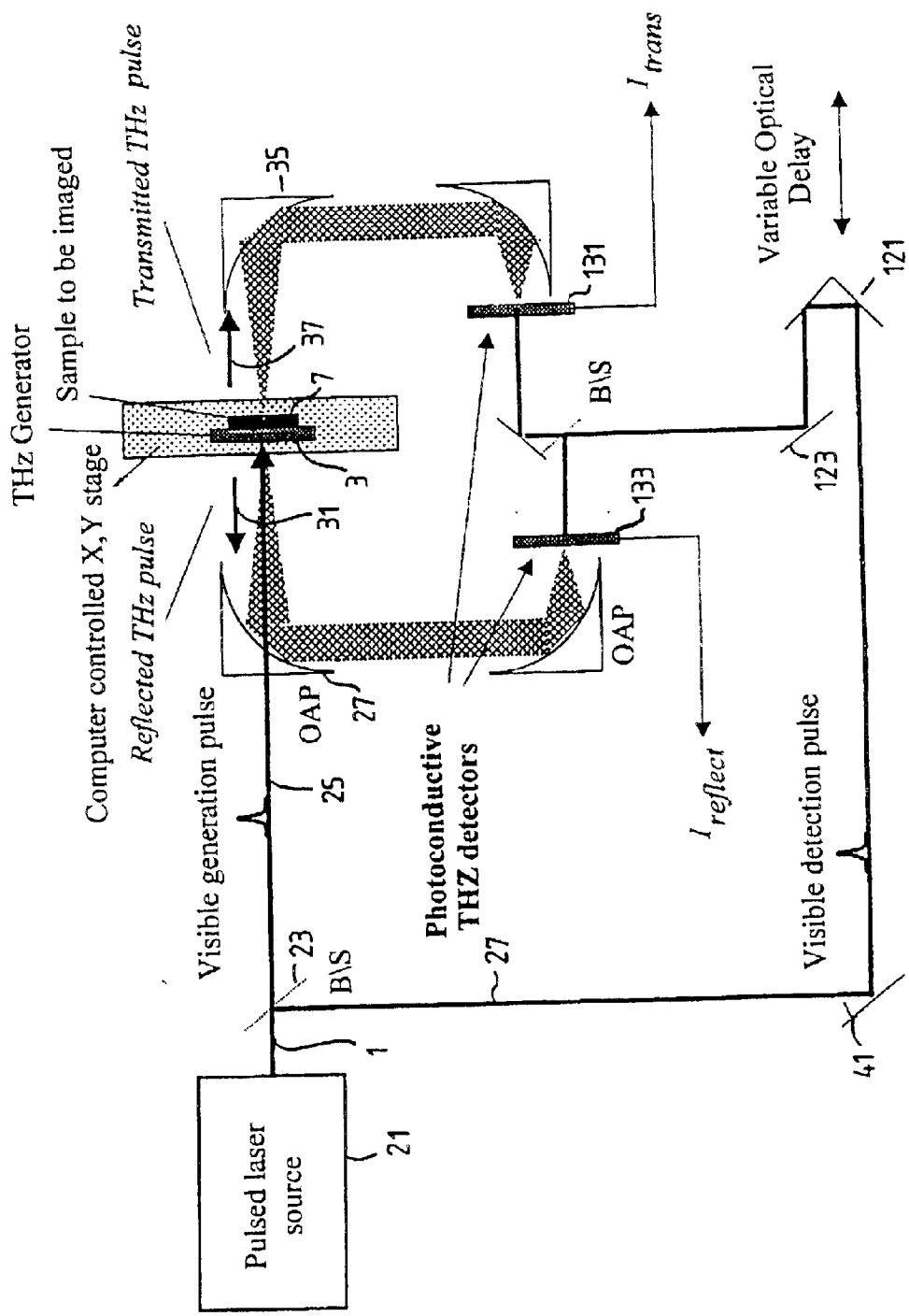
FIG. 5 shows the imaging system of FIG. 2 with details of the detectors.

FIG. 5 shows a variation on the system of FIG. 4. Here, photoconductive detection by photoconductive THz detectors 131 and 133 are used to detect the transmitted and reflected THz beam.

The system shown in FIGS. 4 and 5, the systems have a single optical delay line (which is achieved by cube mirror 121 and plane mirror) that services both detection elements. Alternatively, a separate delay line for each detection element could be used. This may be necessary when very thick objects are imaged. Here, the transmitted THz pulse would experience a longer delay than the pulse reflected from the front surface. Hence, a single optical delay may not be suitable.

The off axis parabolic mirrors 29, 35 need to be carefully aligned to ensure efficient collection of both the transmitted 37 and reflected 31 THz beams.

If a THz beam is incident on a curved surface, i.e. one with a surface normal not parallel to the direction of the THz beam, the THz beam will not be reflected along the same axis. Instead, it will be reflected at an angle which increases with the surface curvature.

In the two above THz detection methods, the THz is focused to a point for detection, thus information about the path the different THz beams take following reflection can be lost.

Also, when collecting the output using an off axis parabolic mirror, there is a slight time delay due to the different optical path lengths between the centre and the fringe and the mirror. Consequently, the different path lengths reflected beams would cause the pulses to arrive at different times at the detector. Using the detection methods of FIGS. 4 and 5, the beams are focused to a single point. This causes a problem as it is difficult (if not impossible) to discriminate between a time shift due to the opposition of dielectric layer and a time shift that is a combination of the dielectric position and a different paths length on the mirror. The effects of different paths to the mirror are greatest when the surfaces/interfaces are sharply curved. However, if using a CCD camera both the temporal and spatial shift of the THz beam can be measured and this allows the exact curvature of the sample pixel by pixel to be determined.

Figure 6:
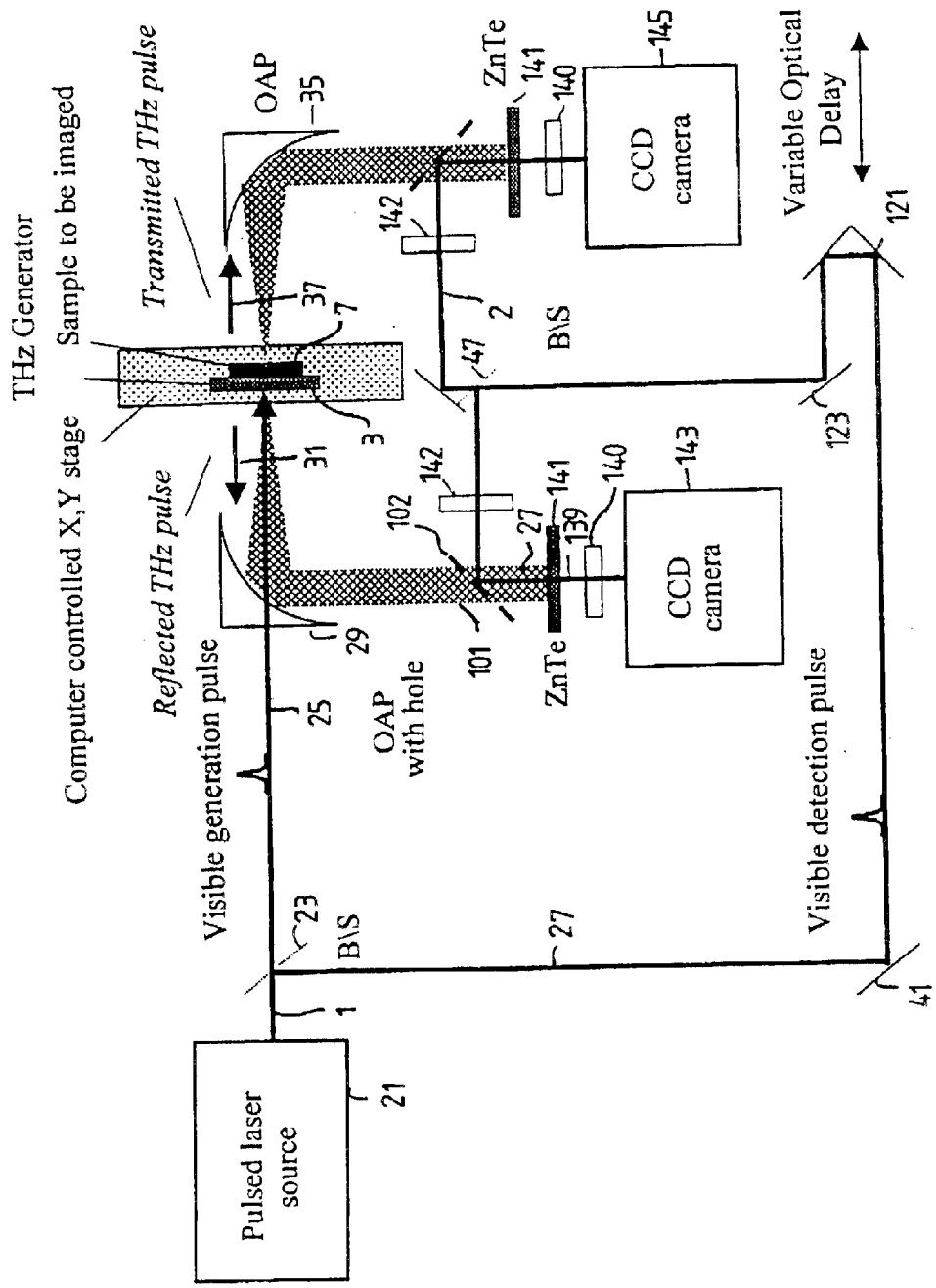
FIG. 6 shows the imaging system of FIG. 2 with details of the detectors.

FIG. 6 shows a similar system to that of FIGS. 4 and 5. The difference is that the detection mechanism of FIG. 6 uses a CCD.

The reference beam 27 is reflected off mirror 47 and is polarised by passing the beam through polariser 142. The polarised reference beam 27 is then combined with the reflected radiation 101 using beam splitter 102. The beam splitter is transparent to THz radiation and hence THz radiation is transmitted through beam splitter 102. However, it is not transparent to visible light and hence the reflected polarised reference beam 27 is combined with the THz beam. The reflected THz beam 101 and the reference beam 27 are directed toward detector crystal 141. This detection mechanism is based on AC Pockles effect and the polarisation of reference beam 27 is rotated by the presence of reflected THz beam 101. The emergent beam 139 is then passed through polariser 140. Polarisers 140 and 142 are crossed relative to each other. Therefore, if no THz beam is present, the polarisation of beam 27 is not rotated and hence the beam is blocked by polariser 140. However, if the beam is rotated, polariser 140 will transmit at least a part of the transmitted beam 139. The output of output 140 is then directed to CCD camera 143. Hence, CCD camera 143 is used to detect the presence of THz radiation and it also gives the spatial dependence of the reflected THz beam via the spatial variations detected by the CCD.

Figure 7:
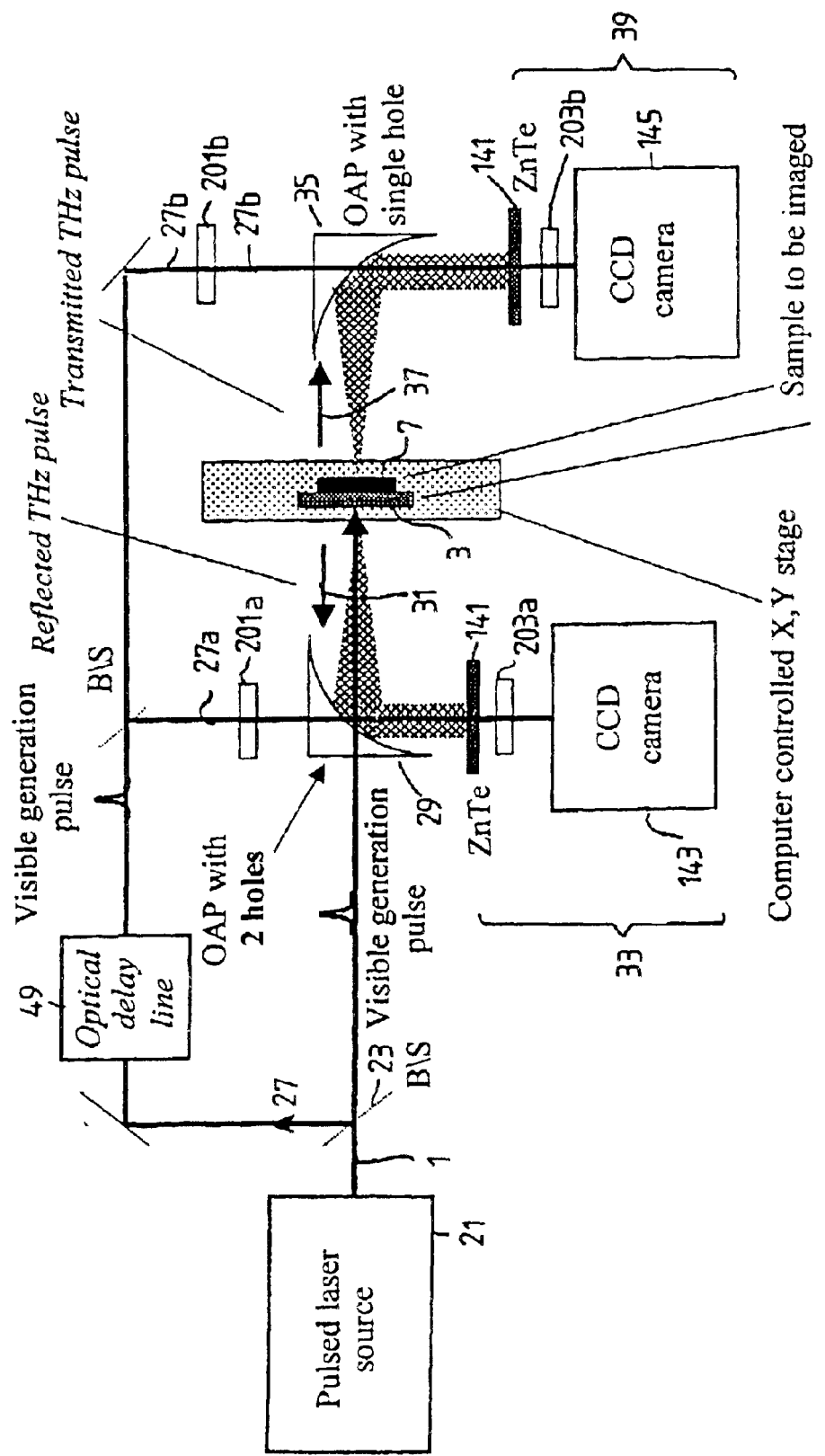
FIG. 7 shows a variation on the imaging system of FIG. 6.

FIG. 7 shows a variation on the system of FIG. 6. The system of FIG. 7 is more compact than that of FIG. 6. The visible input beam 23 is transmitted onto the emitter 3 through a hole in off axis parabolic mirror 29 in the same manner as described with reference to FIG. 1. Off axis parabolic mirror 29 is used to collect the reflected radiation and directed into detector 33. Similarly, the transmitted radiation is collected by off axis parabolic mirror 35 and is directed into detector 39.

The main difference between this system and the system of FIG. 6 is the way in which the reference beam is combined with the reflected and transmitted THz beams. The reference beam 27 is fed through an optical delay line 49 as previously described. The part of the beam 27a which is to be used for the reflected THz signal is passed through a first crossed polariser 201a. This polarised reference beam is then passed through a second hole in off axis parabolic mirror 29 such that the reflected THz pass 31 and the polarised reference signal 27a are both directed into the detector 33. In the same way as described with reference to FIG. 6, the THz beam 31 causes rotation of the polarisation of the reference beam 27a. A second polariser 203 a blocks the path of any radiation which has not been rotated. 201a and 203a are crossed polarisers. The beam is then fed into CCD camera 143.

The reference beam for the transmitted beam is split off as beam 27b. This beam is then passed through polariser 201b to obtain a polarised reference beam. The beam 27b is then passed through a hole in off axis parabolic mirror 35 to combine the transmitted THz radiation 37 with the reference beam 27b. The presence of the transmitted THz is then detected via rotation of the polarisation of the reference beam 27b as described previously. The emergent beam is then fed into polariser 203b. Polariser 203b is crossed with polariser 201b such that polariser 203b blocks any radiation which has not had its polarisation vector rotated.

Figure 8:
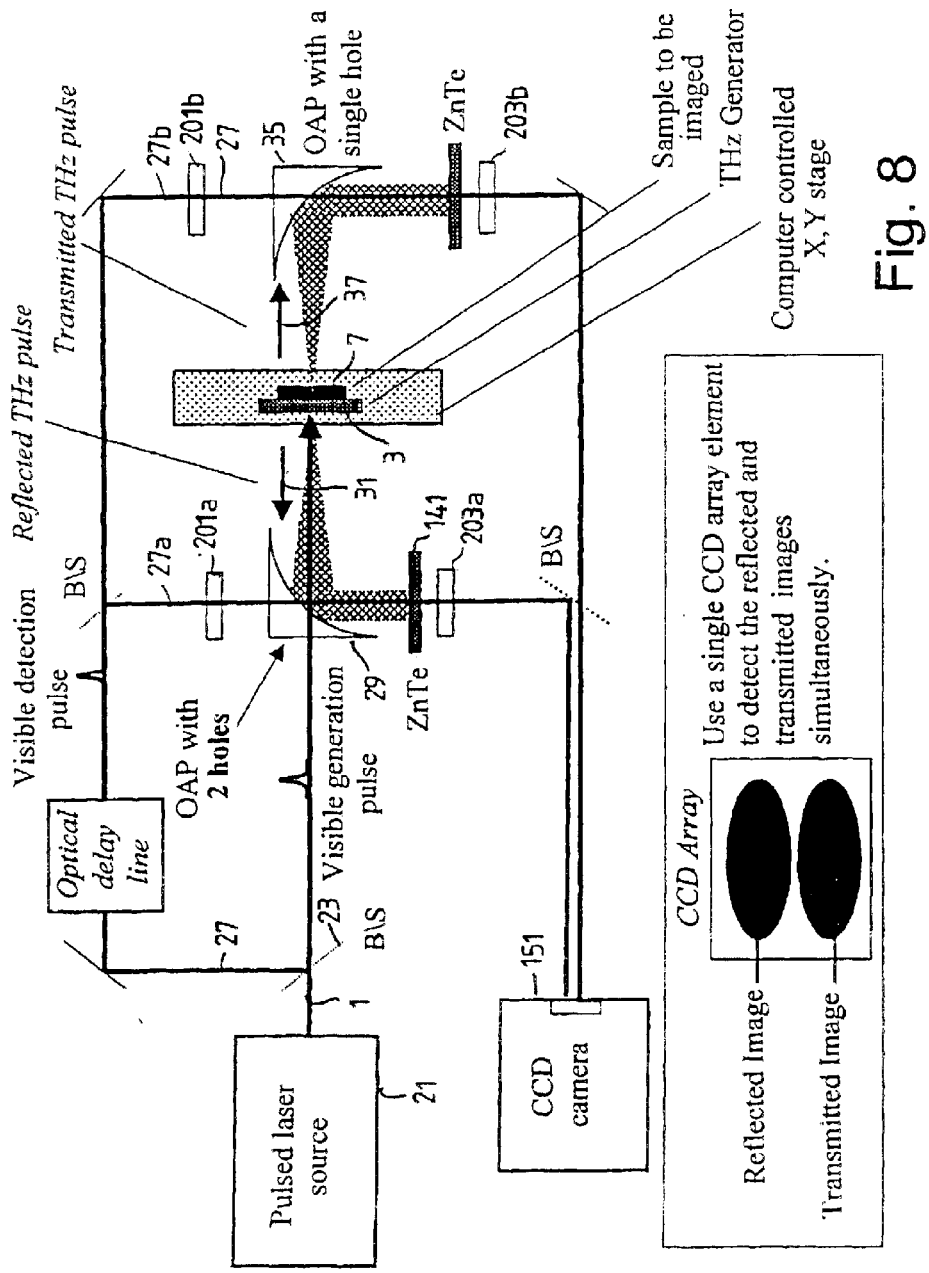
FIG. 8 shows a variation on the imaging system of FIGS. 6 and 7.

FIG. 8 shows a very similar system to that of FIG. 7. Here, though instead of two CCD cameras 143 and 145 a single CCD camera 151 is used to detect both the transmitted and the reflected radiation. Specifically, the beam which is transmitted by second cross polariser 203a is directed into CCD camera 151. Also, the beam which is transmitted by second crossed polariser 203b (transmitted radiation) is also directed into CCD camera 151. The use of the single CCD array element means that reflected and transmitted images are detected simultaneously.

Figure 9:
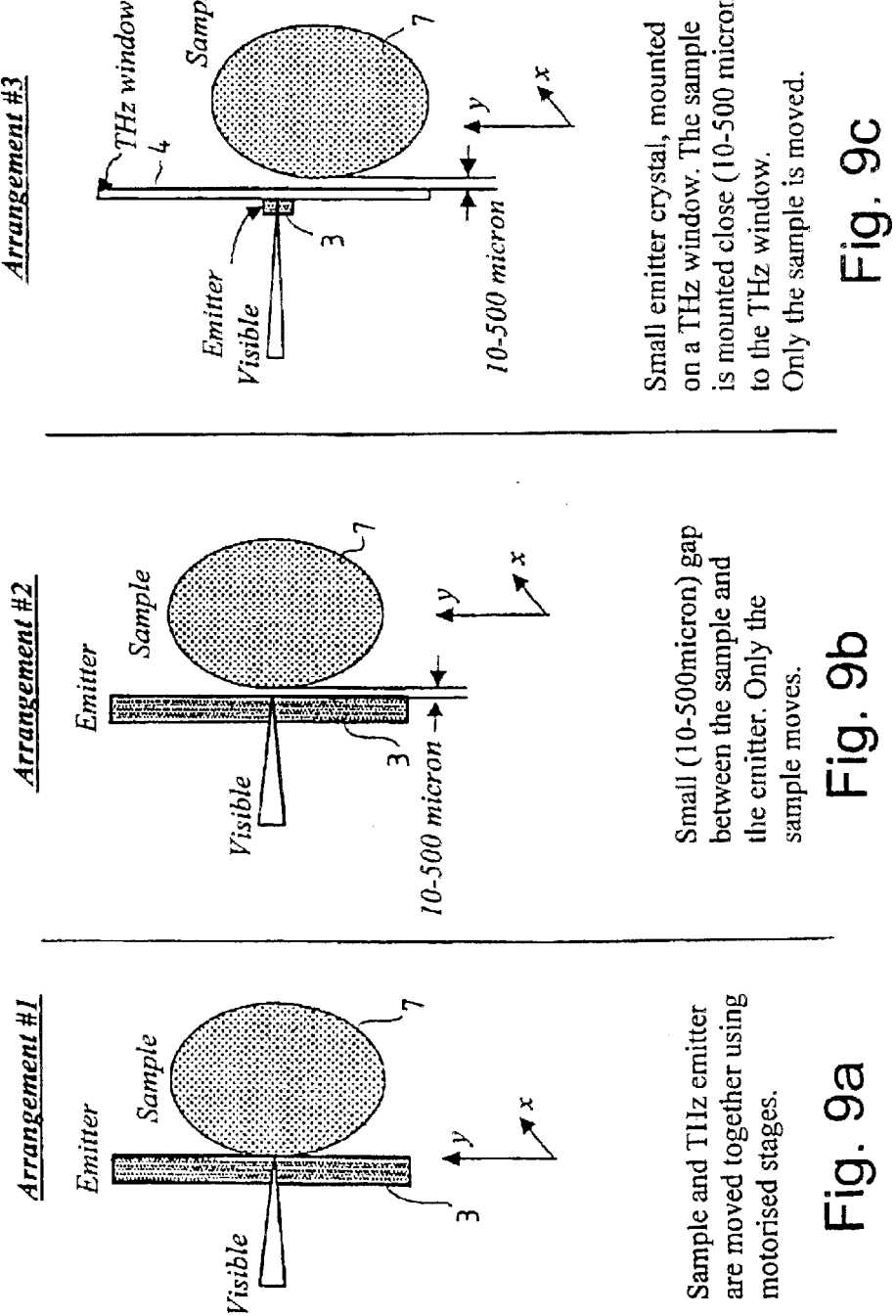
FIGS. 9a, 9b and 9c show three variations on the method of mounting the sample to be imaged.

In FIGS. 1 to 8, the sample is shown actually mounted on the emitter. This arrangement is specifically shown in FIG. 9a. To obtain a full image of an area of the sample, the sample is stepped relative to the THz beam in both the x and y directions, pixel by pixel. This can be done by mounting the sample on the emitter and moving both the emitter and the sample together using the motorised stage.

In the imaging system, both reflected and transmitted radiation must be collected. Therefore, the reflected THz pulses have to be passed back through the emitter crystal before reaching the off axis parabolic mirror (reference numeral 29 in FIGS. 1 to 8). In other words, the emitter acts as a window for the reflected THz. Also, to allow a large range of sample sizes and surface curvatures to be measured, the emitter must also be sufficiently large to allow all of the reflected beams to pass back through it.

FIG. 9b shows an arrangement which allows a smaller emitter to be used. In this arrangement, the sample is mounted in close proximity to the emitter (for example, between 10 and 500 $\mu$m and only the sample is moved in the x-y planes). In other words, the sample is moved relative to the emitter. To ensure high spatial resolution (i.e. in the near field region), the sample must be kept close to the emitter surface. Also, the sample may be mounted on a thin window which is in turn mounted about 10 to 100 $\mu$m from the surface of the emitter 3. In this case, the emitter still needs to be large enough to permit all the reflected pulses from the sample to reach the off axis parabolic mirror 29. The required emitter size in the arrangement of 9b is smaller than that of 9a as in 9a, the emitter needs to be big enough to catch all reflections from the sample. In the arrangement in 9b, the emitter just needs to be big enough to catch all reflections from the small part of the sample being imaged.

In FIG. 9c, the emitter is mounted on a THz window 4. As the mount for the emitter transmits THz, the emitter can be made even smaller as there is no requirement now for all of the reflected THz pulses to pass back through the emitter. The emitter just needs to be big enough to produce the THz beam. Again, the sample is mounted in close proximity to the emitter as opposed to onto the emitter. In this arrangement, only the sample needs to be moved. Therefore, the emitter only needs to be a few millimetres square in area (for example, less than 25 mm by 25 mm). The window 4 is thin (between 50 μm and 300 μm) to ensure that the THz beam diameter is still smaller than the shortest wavelength component when it reaches the sample.

Figure 10:
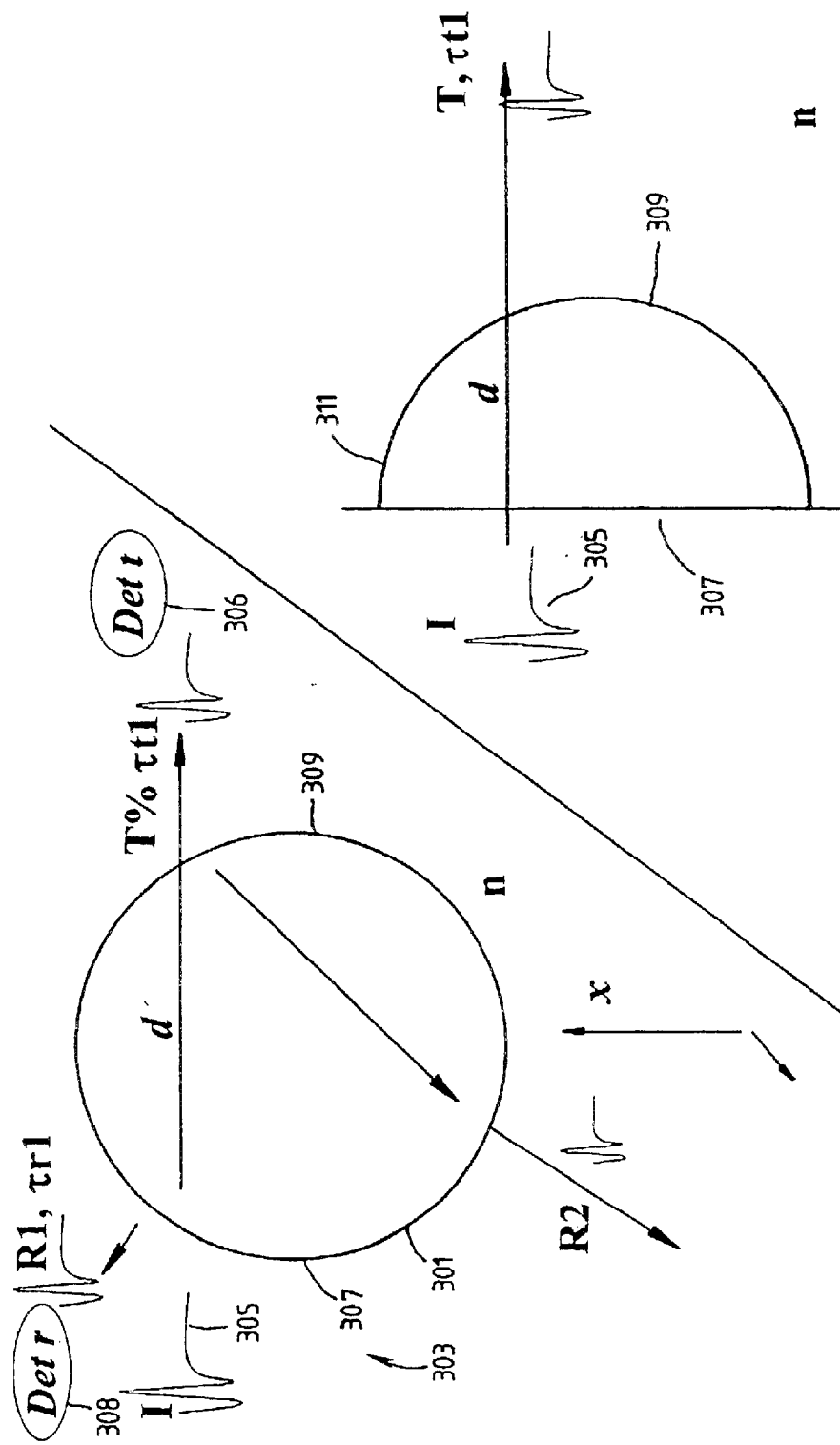
FIG. 10 shows a schematic of a uniform sphere for explaining a method in accordance with an embodiment of the present invention.

FIG. 10 shows a uniform sphere 301 which will be used as a simplified example for explaining the principles of the present invention. Sphere 301 is formed of a dielectric material such that there is a difference in the refractive index at the THz frequencies between the sphere 301 and the space in which is it located 303.

The thickness of a dielectric layer d can be deduced from the time delay τ using the relation.

$$\tau = d(n-1)/c \qquad (1)$$

where n is the index of refraction of the medium through which the radiation penetrates and c is the speed of light in free space.

Thz beam 305 is incident on sphere 301. THz beam 305 is transmitted through sphere 301 (shown as beam T1) and collected by transmitted radiation detector 306. The beam is also reflected from first interface 307 (beam R1) and second interface 309 (beam R2). For the purpose of this explanation the interfaces are numbered in the order in which they are encountered by the beam of radiation 305. The reflected THz beam is collected by reflected radiation detector 308.

The time delay $\tau_{t1}$ of transmitted beam T1 can be used to determine the thickness of the sample. However, it is not possible to determine whether the object is spherical (circular) or rectangular, or any other shape, because $\tau_{t1}$ is the same for all shapes of equal thicknesses. For example, shape 311 has the same thickness as sphere 301. However, the front interface 307 of shape 301 is flat. Both sphere 301 and shape 311 will give rise to the same time of flight of the transmitted signal.

To establish the shape of the object, the time delay associated with the pulse reflected R1 off first surface 307 is required. This is measured by reflected THz detector 308. The time of flight of this pulse $\tau_{r1}$ establishes the position of the first dielectric interface (e.g. air-sphere). From this, the position of the second interface 309 can be determined as the thickness of the sample 301 is known from $\tau_{t1}$.

Therefore, by plotting the difference $\tau_{t1}-\tau_{r1}$ at each pixel co-ordinate (x,y) relative to $\tau_{r1}$ at that pixel, one may plot out the shape of sphere 301.

The absolute position of the object may be established by plotting $\tau_{r1}$ relative to another reflection from a reference plane of known position, for example the top or bottom surface of a window transparent to Terahertz (not shown in FIG. 1), and placed between the incident beam 305 and the sample 301 or an internal reflection in the Terahertz emitter itself (also not shown in FIG. 1).

In theory, it is possible to trace out the shapes in a similar fashion by using the time of flight $\tau_{r2}$ of the pulse R2 reflected off the sphere-air first interface 309. However, there are two reasons why this is often not practical. Firstly, the pulse R2 is likely to be weak due to attenuation as it travels through the sphere. This is especially true in a sample such as a human tooth, where dentine, enamel, and the cavity pulp all absorb Terahertz. Secondly, the curved nature of the sphere-air interface 309 dictates that the reflected signal R2 is likely to fall outside the field of view of the detector. The signal R1 is closer to the detector 308 and can be more efficiently collected. This point is even more of a limitation in objects of arbitrary shape, where the back surface is curved or contoured, and it is thus difficult or impossible to judge what angle R2 is likely to be reflected through with no α priori knowledge of the back surface 309.

The transmitted signal T1 is superior to R2 in this case because 1) the transmitted signal is likely to be stronger than R2 because it has traversed the sphere only once and its attenuation is therefore less than R2, and 2) the transmitted radiation detector 306 can be accurately placed quite close to the object and hence collect all the radiation T1.

Figure 11:
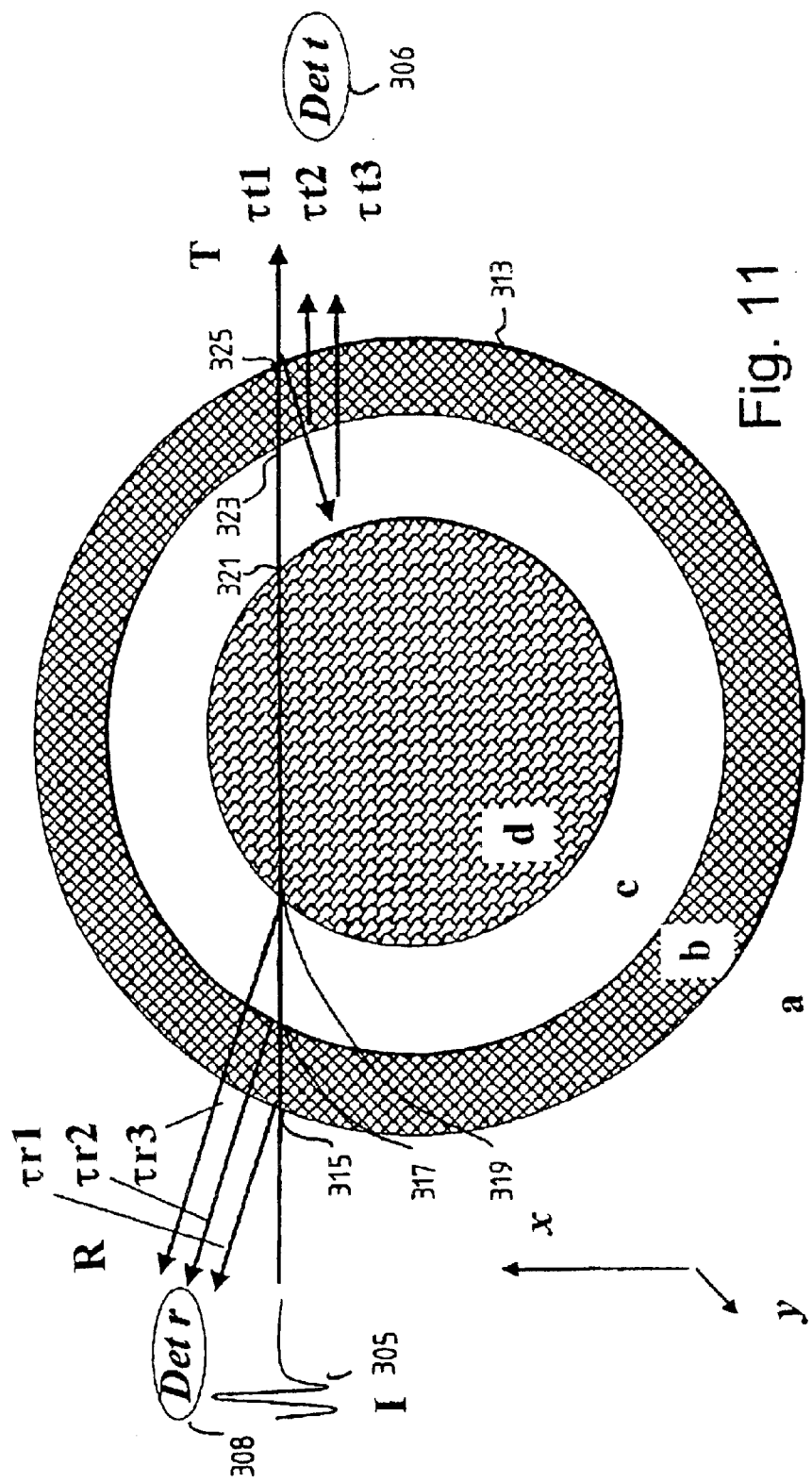
FIG. 11 shows a schematic of a sphere having a plurality of internal interfaces for explaining a method in accordance with an embodiment of the present invention.

The sphere of FIG. 10 was uniform with no internal interfaces. The situation is more complicated where there are a plurality of internal interfaces. FIG. 11 shows a more general case of FIG. 10, where 3D sample 313 comprises a plurality of concentric dielectric spheres. The sample is located in free space 'a'. The sample has an outermost sphere 'b', a middle sphere 'c' and an inner sphere 'd'. In general, each sphere will have a different absorption coefficient and refractive index.

In a manner similar to that described with reference to FIG. 10, the sample 313 is irradiated with THz radiation 305. The transmitted radiation is collected using reflected radiation detector 308. Initially, the signal collected by the reflected radiation detector will be discussed.

To construct an image with absolute co-ordinates, a reflection from a reference plane of known position is required, for example the top or bottom surface of a window transparent to Terahertz and placed between the incident beam 305 and the sample 313 (not shown), or an internal reflection in the Terahertz generation crystal (not shown).

The three of the strongest signals detected by reflected radiation detector 308 will be the reflection from the from a-b interface 315, the reflection from the b-c interface 317 and the reflection from the c-d interface 319.

The position of the a-b interface 315 can be determined by measuring the time delay $\tau_{r1}$ associated with pulse reflected from interface 315. Comparing $\tau_{r1}$ to time delay associated with the pulse reflected from a reference plane (not shown), the position of the interface a-b can be determined.

The position of the b-c interface 317 can be determined by measuring the time delay $\tau_{r2}$ associated with pulse reflected from the interface 317. By comparing this to time delay associated with the pulse reflected from a-b interface 315, the position may be obtained by plotting the thickness determined from $(\tau_{r2}-\tau_{r1})c/2n$ relative to the position determined from $\tau_{r1}$.

In determining the position of b-c interface 317, the refractive index n of region b should be used to correct for material contributions to the $\tau_{r2}-\tau_{r1}$. 'c' is the speed of light in free space (n=1).

The position of the c-d interface 319 can be determined by measuring the time delay $\tau_{r3}$ associated with pulse reflected from the interface 319. By comparing this to time delay associated with the pulse reflected from b-c interface 317, the position can be obtained by plotting the thickness determined from $(\tau_{r3}-\tau_{r2})c/2n$ relative to the position determined from $\tau_{r2}$. In determining the position of interface b-c, the refractive index n of region c should be used to correct for material contributions to the $\tau_{r3}-\tau_{r2}$. 'c' is the speed of light in free space (n=1).

The position of the 'deeper' interfaces d-c 321, c-b 323, and b-a 325 are determined using the data collected by detected transmitted radiation detector 306.

In order to use reflection and transmission data together, it is necessary to establish a common time zero, and the plot the various delay times $\tau_{r1}$, $\tau_{r2}$ . . . , and $\tau_{t1}$, $\tau_{t2}$, after this time zero. Time zero can be taken as $T_{ref}/2$ $T_{ref}$ is the time at which the reference pulse reaches the reflected radiation detector 308. This is essentially time at which the incident pulse 305 leaves the reference plane and travels towards the sample 313.

The next step in constructing the 3D image is to plot the position of the interface d-c 321 (unknown) relative to the position c-d 319 known from the reflection analysis above. This involves using the time delay between the beam reflected from c-d interface 319 and transmitted from interface d-c 321.

Radiation transmitted through the sample will undergo multiple reflections before it is transmitted. The signal due the radiation which has not undergone multiple reflection and has just passed through the sample 313 is t1. The time of flight of t1 through the sample is $\tau_{t1}$.

Transmitted beam t2 which is detected by transmitted radiation detector 306 has been transmitted through interfaces 315, 317, 319, 321 and 323. However, the beam is reflected back into the sample 313 at b-a interface 325. t2 is reflected for a second time by c-b interface 323 and exits the sample 313 to be collected by transmitted radiation detector 306. The time of flight of beam t2 is $\tau_{t2}$.

Transmitted beam t3 which is detected by transmitted radiation detector 306 has been transmitted through interfaces 315, 317, 319, 321 and 323. However, the beam is reflected back into the sample 313 at b-a interface 325. t3 is transmitted through interface 321 and is reflected for a second time by d-c interface 321 and exits the sample 313 to be collected by transmitted radiation detector 306. The time of flight of beam t3 is $\tau_{t3}$.

Transmitted beam t3 undergoes multiple reflections before it is detected and therefore incurs additional delays, it is necessary to correct for these additional delays. For the transmitted pulse 3, one wants to know at what time $t_{t3}'$ the transmitted pulse first passed through the interface d-c 321.

The time $\tau_{t2'}$ at which the pulse passed through interface c-b is calculated from $$\tau_{t2}' = \tau_{t1} - (\tau_{t2} - \tau_{t1})/2.$$

The time $t_{t3}'$ at which the pulse passed through interface d-c is calculated from $$\tau_{t3}' = \tau_{t2}' - (\tau_{t3} - \tau_{t2})/2.$$

The position of d-c can now be obtained by plotting the thickness obtained from $(\tau_{t3}' - \tau_{r3})c/n$ relative to the position of interface c-d determined from $\tau_{t3}$ (see above). In determining the position of interface d-c, the refractive index n of region d should be used to correct for material contributions to the $\tau_{t3}' - \tau_{r3}$ in this context is the time at which reflected pulse 3 is reflected from the interface c-d relative to reference time zero.

The position of c-b can be obtained by plotting the thickness obtained from $(\tau_{t3} - \tau_{t2})c/2n$ and adding this to position obtained from $\tau_{t3}'$ above. Materials contributions from the refractive index n of region c are also included.

The position of b-a can be obtained by plotting the thickness obtained from $(\tau_{t2} - \tau_{t1})c/2n$ and adding this to position obtained from $\tau_{t2}$ above. Materials contributions from the refractive index number of region b are also included.

Figure 12:
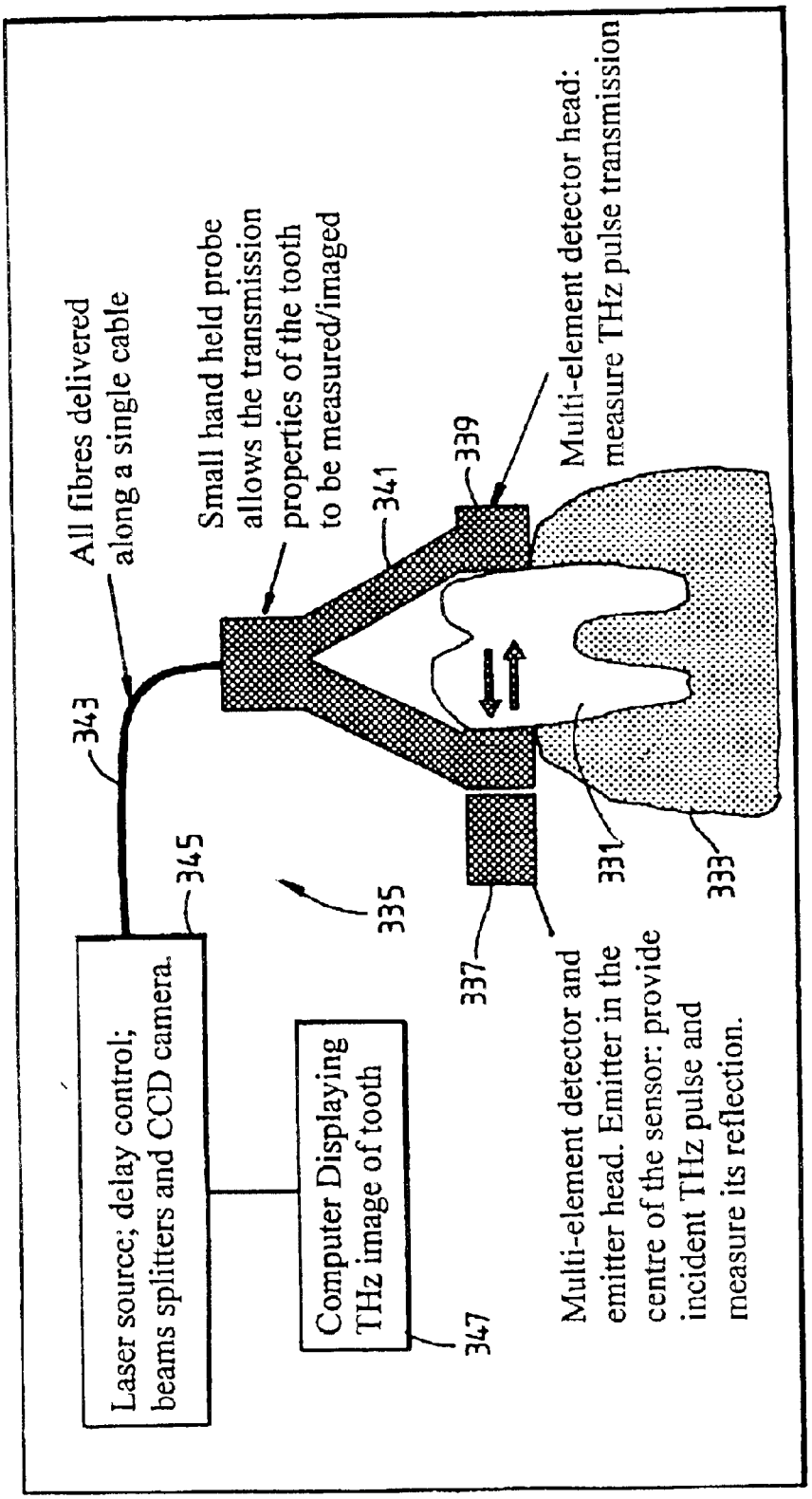
FIG. 12 shows an embodiment of the present invention used for imaging a tooth.

FIG. 12 shows how such a system might be implemented technologically to scan a tooth.

The sample is tooth 331 which is a living tooth and is located in gum 333. The tooth is imaged using THz 3D imaging system 335. The THz 3D imaging system comprises a THz emitter/detector 337 which emits the THz radiation and also serves to detect reflected THz addition in the same manner as that described with reference to detector 308 in FIGS. 10 and 11. Radiation transmitted through the tooth 331 is detected by transmitted THz radiation detector 339 which is used to collected the radiation in the same manner a detector 306 described with reference to FIGS. 10 and 11.

The details of the THz emitter/detector 337 and the detector 339 will not be described here. However, an arrangement as described with reference to any of FIGS. 1 to 9 could be used. In the specific example shown in FIG. 12, multi element detectors are used to detect both the transmitted and reflected radiation. This means that there is not need to scan the beam or the sample as the detectors are configured to collect transmitted or reflected radiation from all of the required pixels at the same time.

The multi-element head is formed from a plurality of fibre optic cables configured to collected the transmitted or reflected radiation. Information carried by the detected THz radiation may be converted into another form at the probe prior to transmitting away form the probe for analysis. For example, the THz frequency may be stepped up for transmission. Alternatively a reference beam may be supplied to the detector and the AC Pockels effect may be used to allow rotation of the polarisation of the reference beam in accordance with the detected THz signal as described with reference to FIGS. 4 and 6. The reference beam with the rotated polarisation vector can then be transmitted away from the probe using a polarising preserving fibre for each element pixel of the detector.

The detector/emitter 337 and the emitter 339 are located on probe 341. The probe is 'Y' shaped such that the tooth 331 is located between the arms of the Y when the probe is n position on the tooth 331. The detector/emitter 337 and the detector 339 sit at the end of the arms of the 'Y' on either side of the tooth 331.

A fibre optic cable 343 is connected to the top of the inverted 'Y' of probe 341. Cable 343 carries radiation to the probe 341 for imaging and also carries information away from probe 341.

The fibre optical cable 343 is connected to laser source, delay control, beam splitter and CCD camera 345. These have been explained with reference to FIG. 6. This is in turn connected to a computer 347 for displaying the three dimensional image.

The actual data would be analysed in the same way as described with reference to FIG. 11. For example, in FIG. 11, the regions could be designated as follows: a=air, b=enamel, c-dentine, and d=pulp. The inventors have calculated the refractive index for enamel and dentine (3.2 and 2.6, respectively) and pulp (typically 2.0) and hence are able to use the time delay in conjunction with Equation 1 to characterize the thickness and hence position of the various dielectric layers, which in turn allows a 3D image of the tooth (sphere) to be constructed.

What is claimed is:

1. A method of imaging a sample, the method comprising the steps of:
    (a) irradiating the sample to be imaged with an irradiating beam of pulsed electro magnetic radiation with a plurality of frequencies in the range from 25 GHz to 100 THz,
    (b) simultaneously detecting both the radiation transmitted through the sample and the radiation reflected by the sample;
    (c) generating an image of the sample from the radiation detected in step (b).

2. The method of claim 1, wherein step (c) comprises the step of calculating the time of flight of a pulse transmitted through the sample; calculating the time of flight of a pulse reflected from an interface or surface of the sample; and plotting the difference or function of the difference of the time of flight of the transmitted and reflected pulse relative to the time of flight of the reflected pulse.

3. The method of claim 1 wherein step (c) further comprises the steps of extracting the parts of the transmitted pulse which are due to an even number of reflections within the sample, and determining the position of an interface using the signal caused by said even number of reflections.

4. The method of claim 1, further comprising the step of detecting a reference signal obtained from an object having a known separation from either the emitter of irradiating beam or the sample to be imaged.

5. The method of claim 4, wherein the reference signal is obtained from a reflection off a component of the emitter.

6. The method of claim 1, wherein the irradiating beam has a beam diameter smaller than that of the smallest radiation wavelength of the beam.

7. The method of claim 1, wherein the irradiating beam is emitted by an emitter, the emitter being irradiated with at least one input beam of radiation with frequencies in the visible or near infra red frequency range, the emitter being a material with non-linear optical properties.

8. The method of claim 4, wherein the input beam has a beam diameter which is smaller than the smallest wavelength of the beam of pulsed radiation of step (a).

9. The method of claim 7, wherein the emitter is a semiconductor.

10. The method of claim 7, wherein the material with non-linear optical properties is chosen from the group of LiIO3, NH4H2PO4, ADP, KH2PO4, KH2ASO4, Quartz, AlPO4, ZnO, CdS, GaP, GaAs, BaTiO3, LiTaO3, LiNbO3, Te, Se, ZnTe, ZnSe, Ba2NaNb5O15, AgAsS3, proustite, CdSe, CdGeAs2, AgGaSe2, AgSbS3, ZnS, DAST (4-N-methylstilbazolium) or Si.

11. The method of claim 7, where the sample is mounted such that there are no active optical components between the sample and the emitter.

12. The method of claim 7, wherein the emitter is configured to hold the sample.

13. The method of claim 7, wherein the sample is positioned with a separation from 10 mm to 500 mm from the emitter.

14. The method of claim 7, wherein the emitter is of a size such that radiation reflected from the sample can pass back through the emitter.

15. The method of claim 7, wherein the emitter is substantially transparent to the irradiating beam.

16. A method according to claim 1, wherein a CCD camera is used to detect the radiation reflected from and transmitted through the sample.

17. The method of claim 1, wherein a three dimensional image is generated in step (c).

18. The method of claim 1, wherein a compositional image is generated in step (c).

19. An apparatus for imaging a sample, the apparatus comprising:
  a) means for irradiating a sample to be imaged with an irradiating beam of pulsed electromagnetic radiation with a plurality of frequencies in the range from 25 GHz to 100 THz;
  b) means for detecting radiation which is both transmitted through and reflected from the sample; and
  c) means for generating an image of the sample from radiation detected in step (b).

20. The apparatus of claim 19, wherein the means for generating an image comprise means for calculating the time of flight of a pulse of radiation transmitted through the sample, means for calculating the time of flight of a pulse of radiation reflected from an interface or surface of the sample; and means for plotting the difference or a function of the difference in the time of flight of the transmitted and reflected pulse relative to the time of flight of the reflected pulse.

21. The apparatus of claim 19, wherein the means for generating an image of the sample comprise means for extracting the parts of the transmitted pulse which are due to an even number of reflections within the sample, and determining the position of an interface using the signal caused by said even number of reflections.

22. The apparatus of claim 19, further comprising means for generating a reference signal.

23. The apparatus of claim 22, wherein the means for generating a reference signal comprise means for measuring a signal reflected from a component of the means for irradiating the sample.

24. The apparatus of claim 19, wherein the means for irradiating a sample, comprises an emitter for emitting the irradiating beam, the emitter having optical non-linear properties, such that when the emitter is irradiated with an input beam with a frequency in the visible or near infra-red frequency ranges, a beam is emitted with frequencies in the range from 25 GHz to 100 THz.

25. An apparatus according to claim 23, wherein the input beam of pulsed radiation has a diameter which is smaller than that of the smallest wavelength of the irradiating beam.

26. The apparatus of claim 19, wherein the means for detecting the radiation comprises a CCD camera for detecting the reflected radiation.

27. The apparatus of claim 19, wherein the means for generating an image of the sample comprises means for generating a three dimensional image of the sample.

28. The apparatus of claim 19, wherein the means for generating an image of the sample comprising means for generating a compositional image of the sample.

* * * * *